US005571077A

United States Patent [19]
Klearman et al.

[11] Patent Number: 5,571,077
[45] Date of Patent: Nov. 5, 1996

[54] SELF-SUPPORTING FOOT ORTHOSIS WITH PIVOTALLY MOUNTED COVER

[75] Inventors: Jeffrey D. Klearman; Jeffrey J. Bierman, both of St. Louis, Mo.; Kevin Runkle, Midland, Tex.

[73] Assignee: Lake Medical Products, Inc., St. Louis, Mo.

[21] Appl. No.: 324,723

[22] Filed: Oct. 18, 1994

[51] Int. Cl.⁶ ........................................ A61F 5/00
[52] U.S. Cl. ..................... 602/27; 128/882; 128/892; 5/648; 5/651
[58] Field of Search .................. 128/882, 892; 602/23, 27–29; 5/648, 650, 651

[56] References Cited

U.S. PATENT DOCUMENTS

| 4,076,022 | 2/1978 | Walker | 602/27 |
|---|---|---|---|
| 4,998,537 | 3/1991 | Rau | 602/27 |
| 5,020,523 | 6/1991 | Bodine | 602/27 |
| 5,088,479 | 2/1992 | Detoro | 602/27 |
| 5,151,081 | 9/1992 | Williams | 602/27 |
| 5,154,695 | 10/1992 | Farris et al. | 602/27 |
| 5,370,604 | 12/1994 | Bernardoni | 602/27 |

OTHER PUBLICATIONS

Oscar Plus Ankle/Foot Orthosis by OCS, Orthosis Corrective Systems, Inc., tri-fold brochure and Care Plan sheet.
E-Z Boot™, Medi-Key™ Medical Products, Inc., two-sided color brochure.
E-Z Boot™, Protocol for the Therapeutic Foot and Leg Orthotic System, Jan. 1, 1991, 7-page explanation and assessment.

Primary Examiner—Linda C. Dvorak
Attorney, Agent, or Firm—Howell & Haferkamp, L.C.

[57] ABSTRACT

An ankle/foot orthosis is provided including a generally "L" shaped frame secured to a person's ankle region with Velcro® straps or tape. The frame includes an aperture located over the person's heel such that this ulcer prominent area is unobstructed by the frame. A cover, pivotally mounted to the frame, may be positioned over the aperture thereby protecting the heel from inadvertent contact. The cover may also be opened thereby providing access to the heel and enabling treatment of any ulcerous lesions on the heel while the frame is secured to the ankle region. The cover may also be latched with a cover latch in an over-center open position to thereby provide a support for elevating the foot above a supporting surface.

19 Claims, 4 Drawing Sheets

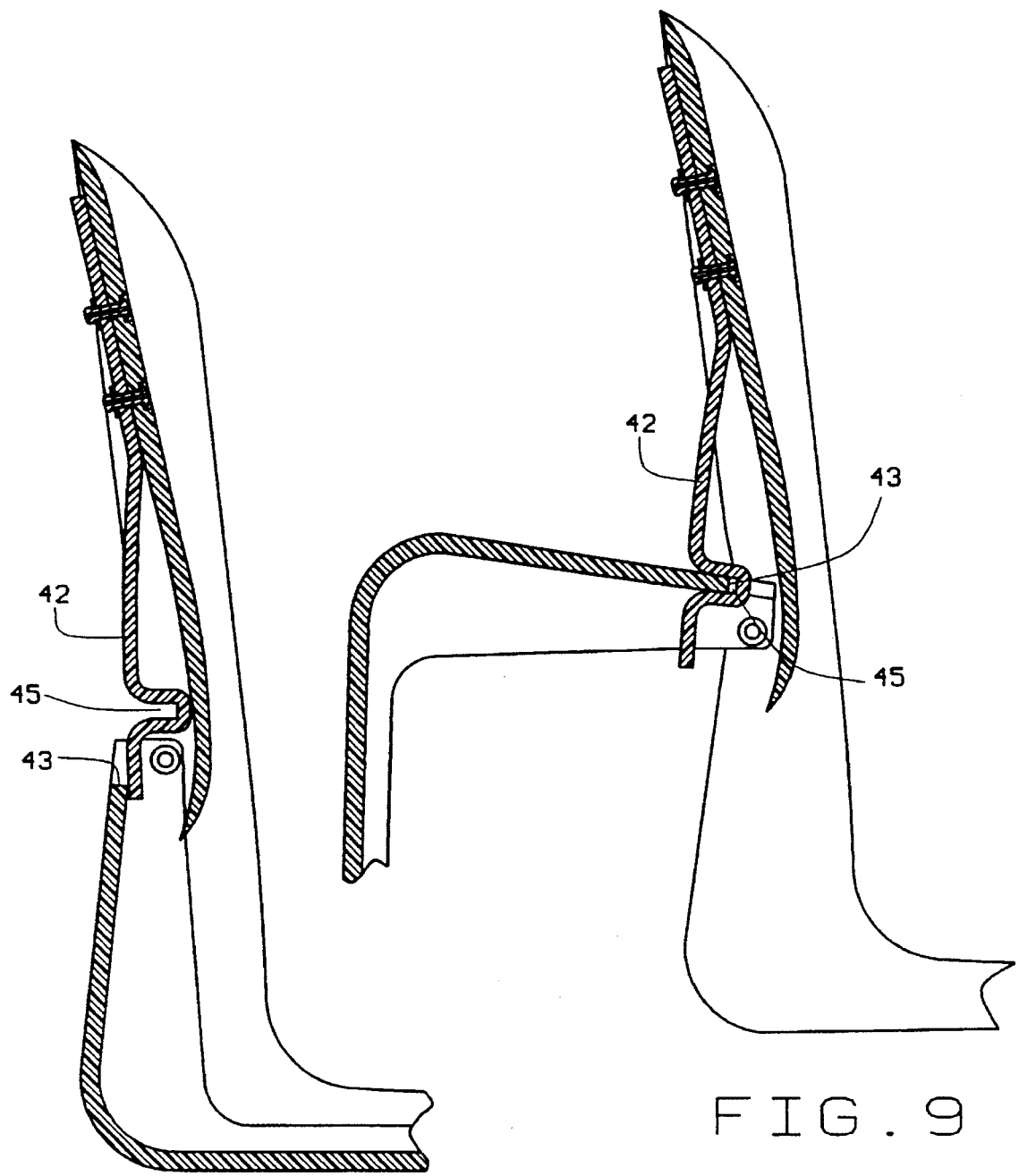

SELF-SUPPORTING FOOT ORTHOSIS WITH PIVOTALLY MOUNTED COVER

BACKGROUND AND SUMMARY OF THE INVENTION

The problem of decubitus ulcers and blisters experienced by people suffering from foot-drop and other nonambulatory conditions is well documented. The primary cause of these ulcers is the immobility of the bedridden patient which causes an interruption in the flow of blood to capillaries in areas of the skin adjacent bone protuberances. The interruption of blood flow to the capillaries causes skin cells to die which results in a breakdown of skin tissue and the development of ulcers. The heel is an area particularly susceptible to decubitus ulcers.

Various ankle/foot orthoses and splints are known in the art for supporting, aligning and correcting foot deformities. For instance, a splint may be chosen for a severely sprained foot or ankle which protects and immobilizes the ankle joint in proper alignment to facilitate healing. Further, persons suffering from paralysis of the anterior leg muscles resulting in insufficient voluntary ankle dorsiflexion (commonly referred to as foot-drop) may select an ankle/foot orthosis which maintains the ankle point in a neutral position and supports the toes while the person is bedridden and/or during walking. While these prior art splints and orthoses adequately support and align the ankle and/or foot, these devices do not address other problems frequently experienced by nonambulatory patients, or patients suffering from foot-drop and other ankle/foot ailments. Nor do these prior art devices provide access for treating (applying ointments or changing dressings) any ulcers without removing the splint/orthosis. Removing the splint/orthosis each time an ulcer is treated is a time consuming procedure and can be quite painful to these patients whose ankle regions are often aggravated and sore. Moreover, because these prior art devices are designed with the singular intention to physically support and align the ankle region, these splints and orthoses often directly contact or are even adhered to the ulcerous area thereby irritating the wound.

Another problem with these prior art devices is that they fail to provide a convenient means for elevating the foot. Elevating an injured extremity is a proven technique to minimize swelling, increase blood circulation, and facilitate the healing process. Several of the prior art splints/orthoses include a mechanism to couple with a traction device thereby enabling elevation of the foot. It is also known to elevate the foot by placing pillows, towels, or books beneath the foot. However, neither of these prior art techniques are convenient for a non-ambulatory person. The former requires specialized traction equipment which is often unavailable except in a hospital setting. Further, spare pillows, books, towels, and other support materials may become undesireably soiled, can be uncomfortable unless care is taken to continuously adjust their positioning, and require a non-ambulatory patient to "ambulate" to fetch the materials or else receive constant attention from others.

In order to solve these and other problems in the prior art, the inventors herein have succeeded in designing and developing an orthosis for supporting a patient's ankle in a neutral position while enabling access for treatment of ulcers on the heel or foot bottom. As used herein "orthosis" shall refer to any device employed to support or align the foot, to prevent or correct foot deformities, or to improve the functions of the foot. Orthoses specifically include splints. The orthosis of the present invention includes a generally "L" shaped frame which is fitted to a patient's foot and back ankle, and is secured with Velcro® straps, tape, or other suitable securing means wrapped around the patient's leg. The frame includes at least one aperture located at the patient's heel such that access to this ulcer prominent region is not obstructed by the frame.

A pivotally coupled cover over the aperture protects any ulcers on the heel from inadvertent contact when closed. By rotating the cover about its pivot, the cover may be swung open to expose the patient's heel thereby allowing treatment of the ulcer without disturbing the frame secured to the patient's leg. This eliminates the time consuming, and often painful, removal of the orthosis as required by the prior art to treat the ulcer. As used herein, "closed" shall refer to the cover positioned adjacent the aperture and "open" shall refer to the cover swung away from the aperture.

Moreover, a biased spring cover latch mounted to the frame allows the cover to be locked in an over-center open position so that the patient may rest his foot with the cover supporting it above any convenient resting surface, such as a bed. Special traction equipment and pillows/books are no longer necessary to elevate a patient's foot as with the prior art. Opening and closing the cover is easily performed by a patient by simply reaching down to the orthosis, operating the cover latch (to open), and rotating the cover about its pivot.

Thus, this invention satisfies a long-felt need by providing an orthosis which sturdily supports an ankle while at the same time allowing heel and foot ulcers to be treated without removing the orthosis, and which provides a stable and convenient mechanism to elevate the foot. While the principal advantages and features of the present invention are briefly described above, a more thorough understanding and appreciation for the advantages and features of the invention may be obtained by referring to the drawings and descriptions of the preferred embodiments which follow.

BRIEF DESCRIPTION OF THE DRAWINGS

FIG. 8 is a partial cross-sectional view of the orthosis of the present invention taken along lines 8—8 in FIG. 4;

FIG. 9 is a partial cross-sectional view similar to that of FIG. 8 illustrating the cover in a locked over-center open position;

DETAILED DESCRIPTION OF THE PREFERRED EMBODIMENT

Figure 1:
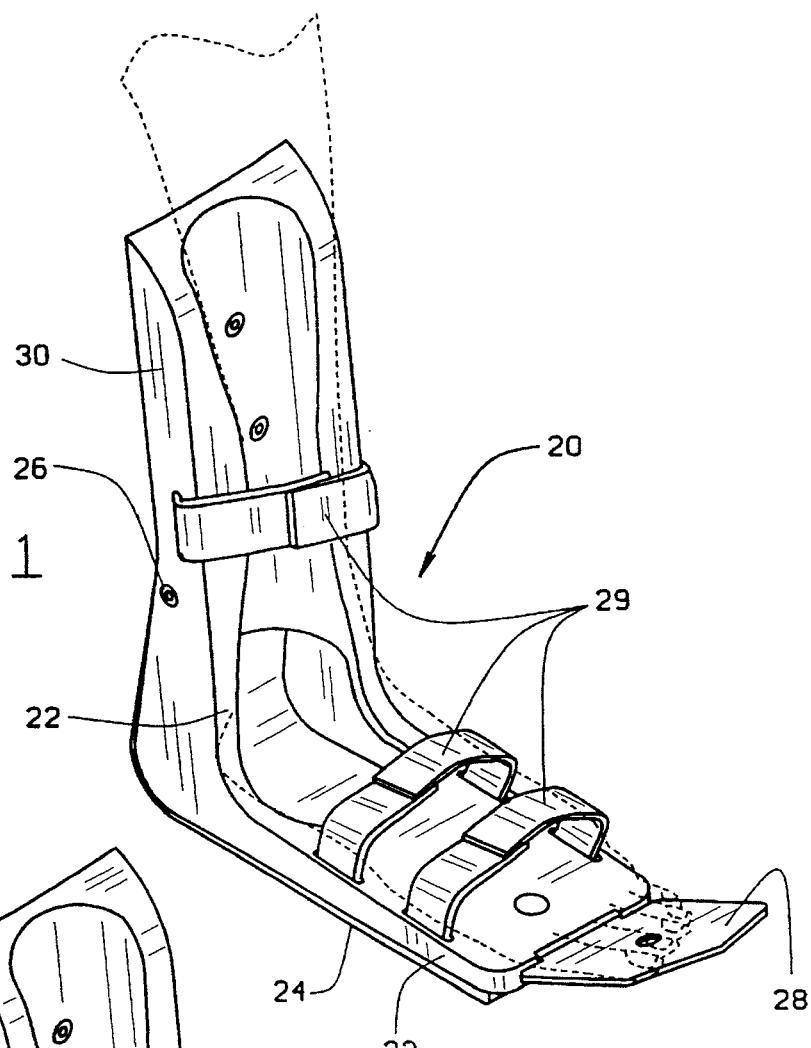
FIG. 1 is an isometric view of the orthosis of the present invention as applied to a patient's foot illustrated in phantom.
Figure 2:
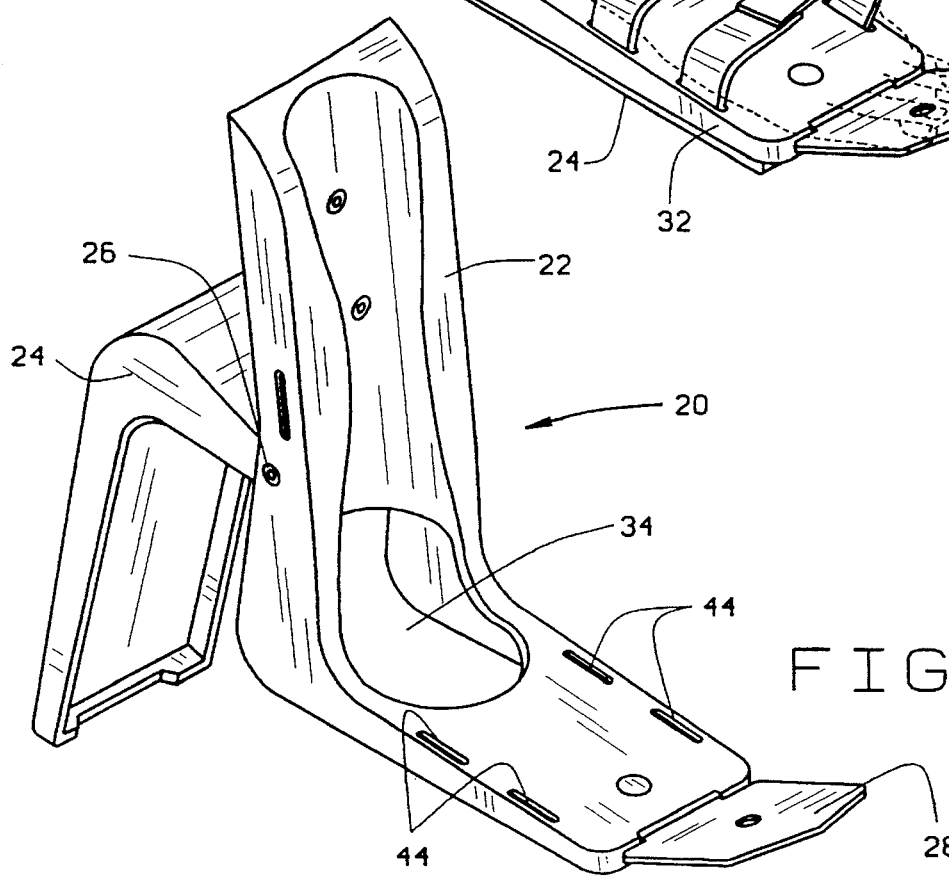
FIG. 2 is an isometric view of the orthosis illustrating the cover latched in an over-center open position.
Figure 3:
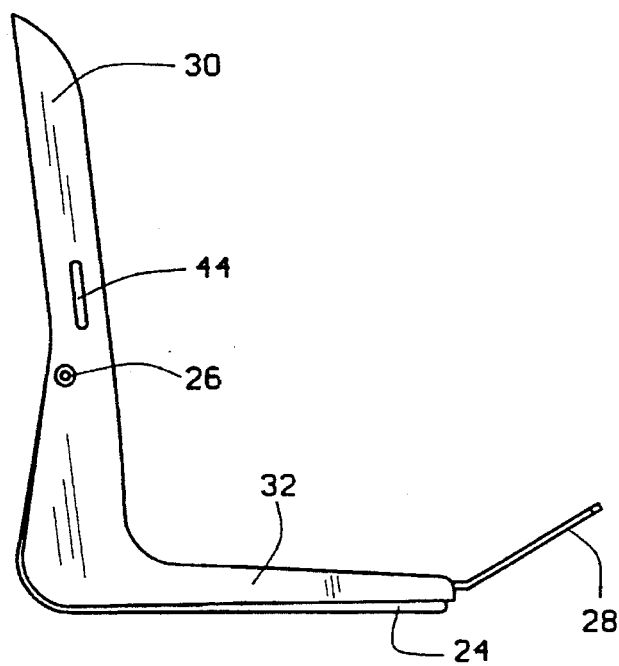
FIG. 3 is a right-side elevation view thereof illustrating the cover closed.
Figure 6:
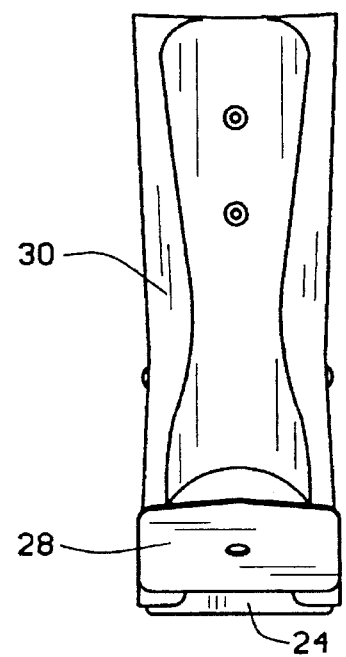
FIG. 6 in an front elevation view thereof.
Figure 4:
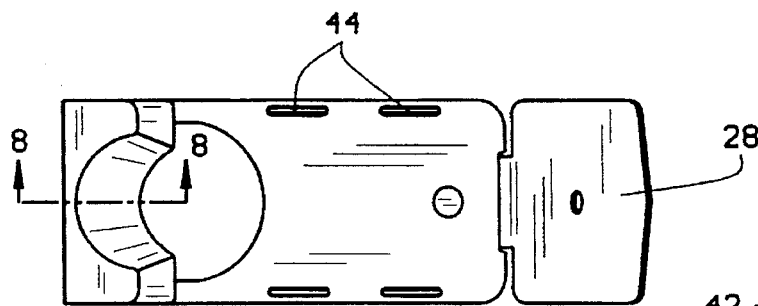
FIG. 4 is a top plan view thereof.
Figure 7:
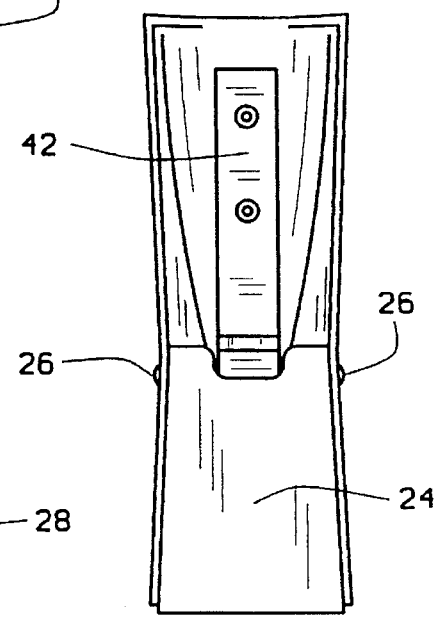
FIG. 7 is a rear elevation view thereof.
Figure 5:
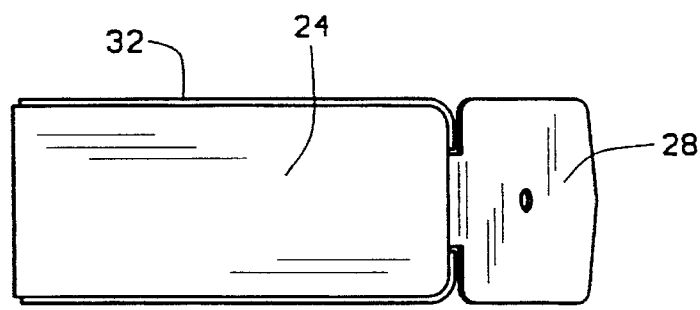
FIG. 5 is a bottom plan view thereof.
Figure 10:
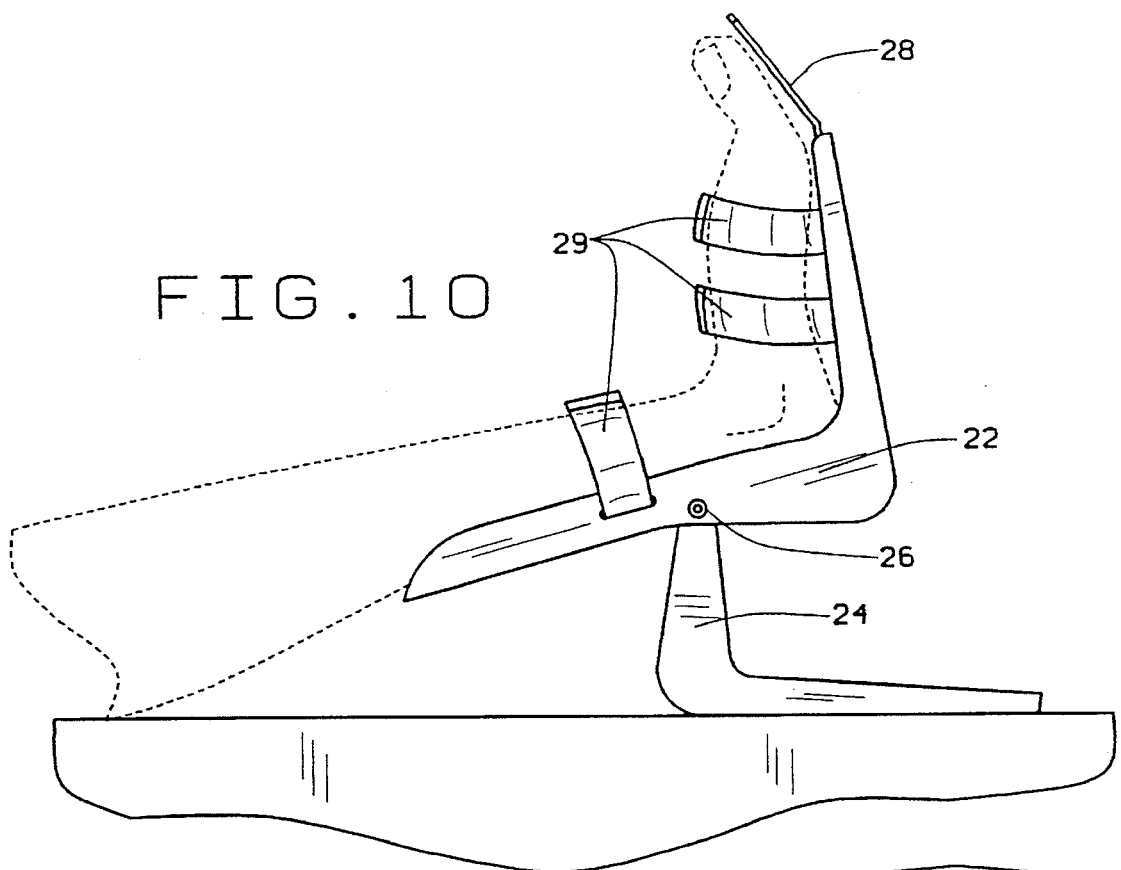
FIG. 10 is a right-side elevation view of the orthosis of the present invention illustrating the cover locked in an open position elevating a patient's foot illustrated in phantom.
Figure 11:
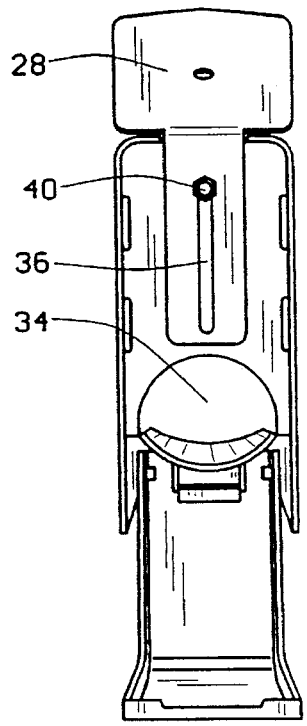
FIG. 11 is a bottom plan view of the present invention with the cover in an open position illustrating the toe platform in a retracted position.
Figure 12:
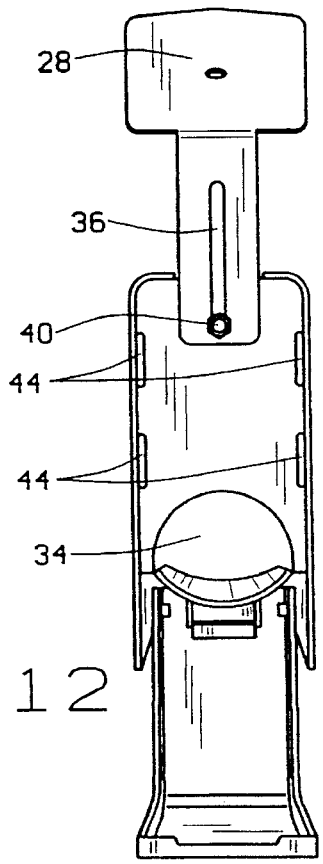
FIG. 12 is a bottom plan view similar to FIG. 11 illustrating the toe platform in a fully extended position.

An orthosis constructed according to the principles of the present invention is indicated generally as 20 in FIGS. 1 and 2. The orthosis 20 includes a frame 22, a cover 24 pivotally coupled to the frame at two pivot points 26, an extendable toe platform 28, and a plurality of Velcro® straps 29 securing the frame to the patient's leg. (See FIG. 10 for an illustration of straps 29). The term "ankle region" shall herein refer to the portion of a human body from the mid-calf to the toes. The frame is generally "L" shaped having a calf section 30 and a foot section 32 conforming generally to the shape of a human ankle region when the ankle joint is in a neutral position. The anterior of calf section 30 is preferably contoured to the shape of a typical human lower calf and Achilles' tendon. The foot section 32 is preferably flat and extends to the metatarsal heads of a typical human foot. An aperture 34 extends through the frame 22 where the calf section 30 and foot section 32 merge for positioning over a patient's heel when the orthosis 20 is properly secured to his ankle region. The toe platform 28 is mounted to the bottom of the foot section 32 and is adjustable by an elongated slot 36 and a pin 40 to accommodate various length feet (See FIGS. 11 and 12). The platform 28 is angled (relative to the foot section 32) to dorsiflex the toes. Of course, the orthosis 20 may be manufactured in various lengths and widths to readily accommodate a wide range of foot sizes.

In the preferred embodiment, the cover 24 is generally "L" shaped and, when in the "closed" position, extends from the pivot points 26 over the aperture 34 to the anterior of foot section 32. In this position, the cover is flush with the lateral sides of the calf section 30 and the foot section 32 and is positioned over the aperture thereby protecting any heel ulcers from inadvertent contact. The cover 24 may be rotated about the pivot points 26 to an over-center "open" position wherein the cover 24 is swung away from the aperture. A spring biased cover latch 42 is mounted to the posterior of the foot section 32 to lock the cover 24 in its open position. Locking the cover 24 in the open position provides a sturdy and convenient means for elevating the ankle region. As shown in FIG. 9, the cover 24 may be swung into an over-center open position and locked in place through an upper edge 43 rotating into a groove 45 in cover latch 42. With edge 43 of cover 24 fitting into groove 45 of cover latch 42, the cover 24 is positively secured in an over-center position with respect to its pivot 26. This helps prevent an inadvertent collapsing of the cover 24 as a patient rests his foot in an elevated position with cover 24 resting against a bed or other supporting surface (See FIG. 10). In order to close cover 24 about frame 22, a patient need only depress cover latch 42 to thereby retract groove 45 which frees the upper edge 43 of cover 24 and permits its pivoting about pivot 26 back into a closed position. As explained, the cover 24 is preferably pivotally coupled to the frame 22. However, it is understood that other coupling techniques may be employed which allow the cover to be removed from the aperture without departing from the scope of this invention. For example, the cover 24 may be snap-fit to the frame 22.

Several pairs of slots 44 are spaced about the frame for accepting the straps 29. It is understood that strips of tape of other suitable material may be substituted for the preferred Velcro® straps to secure the frame to the ankle region. Notice, the slots 44 about the foot section 32 are preferably located through the top of the foot section 32 such that the straps do not interfere with the opening and closing of the cover 24.

In operation, the orthosis 20 is positioned adjacent the ankle region of a person suffering from foot-drop or another ankle/foot ailment. The orthosis 20 is positioned such that the aperture 34 is over the ulcer prone heel section of the foot. The cover 24 is opened and the extendable foot platform is adjusted according to the length of the person's foot. Velcro® straps 29, medical tape, or other suitable straps are placed through the various slot pairs 44 and around the ankle region to thereby securely mount the frame 22 to the ankle region. At this point, the cover 24 is closed thereby covering the aperture 34 and protecting any ulcerous lesions on the heel from inadvertent contact thereby assisting the healing process.

When properly secured to the ankle region, the orthosis 20 supports the ankle region, properly aligns the foot, and maintains the ankle joint in a neutral position much like the orthoses known in the prior art. However, unlike the prior art orthoses, the cover 24 may be opened, thereby exposing the aperture 34 without removing the orthosis frame 22. With the cover in the open position, the heel, and any ulcerous lesions thereon, are easily accessible to a caregiver thereby allowing treatment of the ulcers while the orthosis is secured to the ankle region. Moreover, the cover 24 may be locked in the open position by spring biased latch 42 thereby providing a sturdy mechanism to elevate the foot which is easy to use and convenient for nonambulatory patients. To close the cover, again protecting the ulcer prone heel, the spring biased latch 42 is simply released and the cover 24 is pivoted about the pivot points 26.

In an alternative embodiment, a treaded sole (not illustrated) may be placed on the bottom of the orthosis 20 while the cover 24 is closed thereby facilitating the use of the orthosis 20 as a walking cast. While the frame 22 in the preferred embodiment is a rigid structure, it is understood that the frame 22 could be hinged or pivoted without departing from the spirit or scope of the invention. Moreover, while the aperture 34 is preferably positioned over a patient's heel, it is understood that the aperture may be positioned over the foot bottom and/or various other ankle region locations to facilitate access to ulcerous lesions thereon without departing from the scope of this invention.

In its use, the orthosis of the present invention provides significant improvements over the prior art. The method of using the orthosis of the present invention is also novel and unique and includes the steps of securing the frame 22 to an ankle region such that the aperture 34 is positioned atop the heel thereby not obstructing this ulcer prone area of the ankle region. To treat a heel ulcer, the cover 24 is opened by rotating it about the pivot points 26 thereby exposing the heel while the frame 22 is secured to the ankle region. Additional steps may also be performed as part of the method including locking the cover 22 in the open position by spring biased latch 42 to thereby provide support means to elevate the ankle region.

Although illustrated embodiments of the present invention are described herein with reference to the accompanying drawings, it is understood that the invention is not limited to those precise embodiments and that various other changes and modifications may be constructed therein by one skilled in the art without departing from the scope or spirit of the invention. The scope of the invention is defined solely by the claims and their equivalents, appended hereto.

What is claimed is:

1. An orthosis for supporting a patient's ankle region in a neutral orientation, said orthosis including a substantially L-shaped frame, said frame having an aperture for access to a portion of the ankle region, and a selectably movable cover for said aperture to thereby protect the ankle region portion from inadvertent contact when said cover is in a closed position and to provide access to the ankle region portion when said cover is in an open position.

2. The orthosis of claim 1 wherein said cover is pivotally secured to said frame.

3. The orthosis of claim 2 further comprising a cover latch for locating said cover in an open position.

4. The orthosis of claim 3 wherein said cover latch positively engages said cover when said cover is in said open position.

5. The orthosis of claim 4 wherein said cover latch includes a groove for receiving an edge of said cover.

6. The orthosis of claim 2 wherein said frame includes a heel area, said aperture is located substantially at said heel area of said frame, and said cover is also substantially L-shaped.

7. The orthosis of claim 6 further comprising straps for securing said orthosis to said ankle region.

8. The orthosis of claim 7 further comprising a cover latch for locating said cover in an open position.

9. The orthosis of claim 8 wherein said cover latch positively engages said cover when said cover is in said open position.

10. An orthosis for supporting a patient's ankle region in a neutral orientation, said orthosis including a rigidized, substantially L-shaped frame having a heel section adapted to fit snugly around a patient's heel area, said frame having an aperture extending substantially the width of said frame in the heel section and a substantially L-shaped cover for enclosing said aperture to prevent inadvertent contact with the patient's foot through said aperture when said orthosis is attached to the patient.

11. The orthosis of claim 10 further comprising an adjustable toe platform extending outwardly from a forward end of said frame.

12. The orthosis of claim 11 wherein said toe platform is attached at a point on the bottom of said frame, and said cover extends substantially a full length of said frame to thereby enclose the point of attachment of said toe platform.

13. The orthosis of claim 12 wherein said cover is pivotally secured to said frame.

14. The orthosis of claim 13 further comprising a cover latch for locating said cover in an open position.

15. An orthosis for supporting a patients ankle region in a neutral orientation, said orthosis comprising a frame having an ankle engageable region configured for engaging a rear portion of the the patient's ankle region, and a bracket including a surface-engageable portion, the bracket being connected to the frame for movement of the bracket relative to the frame between a retracted position in which the surface-engageable portion of the bracket is generally adjacent the frame and a propping position in which the surface engageable portion is spaced generally rearwardly of the ankle engageable region for engaging a generally horizontal surface to elevate the patient's foot above the horizontal surface when the patient's foot is oriented with the back of the heel thereof facing generally downwardly.

16. The orthosis of claim 15 wherein said bracket is pivotally attached to said frame for movement between its retracted and propping positions.

17. The orthosis of claim 16 further comprising a latch for engaging said bracket and retaining it in its propping position.

18. The orthosis of claim 17 wherein said latch engages said bracket as it reaches an over-center orientation with respect to its pivotal attachment to said frame.

19. The orthosis of claim 18 wherein said frame and bracket each have members which are substantially parallel to each other when said bracket is in its propping position.

* * * * *

UNITED STATES PATENT AND TRADEMARK OFFICE
CERTIFICATE OF CORRECTION

PATENT NO. : 5,571,077
DATED : November 5, 1996
INVENTOR(S) : Klearman et al.

It is certified that error appears in the above-indentified patent and that said Letters Patent is hereby corrected as shown below:

Title page, item [57]

In the Abstract of the Disclosure, first sentence, replace "Velcro " with --hook and loop--.

In column 6, line 12, delete the second occurrence of the word "the".

Signed and Sealed this

Eighth Day of April, 1997

*Attest:*

BRUCE LEHMAN

*Attesting Officer*  *Commissioner of Patents and Trademarks*